United States Patent [19]
Jones et al.

[11] Patent Number: 5,733,254
[45] Date of Patent: Mar. 31, 1998

[54] METHOD FOR TREATING PATIENTS SUFFERING FROM IMMUNE THROMBOCYTOPENIC PURPURA

[75] Inventors: Frank R. Jones, Edmonds; Joseph P. Balint, Jr., Seattle; Harry W. Snyder, Edmonds, all of Wash.

[73] Assignee: Cypress Bioscience, Inc., Seattle, Wash.

[21] Appl. No.: 432,036

[22] Filed: May 1, 1995

Related U.S. Application Data

[63] Continuation of Ser. No. 171,264, Dec. 21, 1993, abandoned, which is a continuation of Ser. No. 15,327, Feb. 9, 1993, abandoned, which is a continuation of Ser. No. 619,816, Nov. 29, 1990, abandoned, which is a continuation of Ser. No. 290,808, Dec. 22, 1988, abandoned, which is a continuation of Ser. No. 108,530, Oct. 15, 1987, abandoned.

[51] Int. Cl.$^6$ .............................................. A61M 37/00
[52] U.S. Cl. ........................... 604/4; 604/52; 435/7.8; 424/530
[58] Field of Search .................. 604/46, 416, 406, 604/52; 435/269, 7.8; 424/529, 530; 210/638, 632, 264, 195.2, 434

[56] References Cited

U.S. PATENT DOCUMENTS

| | | | |
|---|---|---|---|
| Re. 31,712 | 10/1984 | Giese | 604/5 |
| 3,826,678 | 7/1974 | Hoffman et al. | 604/5 |
| 3,959,128 | 5/1976 | Harris | 604/5 |
| 4,464,165 | 8/1984 | Pollard, Jr. | 604/5 |
| 4,512,763 | 4/1985 | Schneider | 604/5 |
| 4,551,435 | 11/1985 | Liberti et al. | 604/5 |
| 4,581,010 | 4/1986 | Skurkovich | 604/5 |
| 4,614,513 | 9/1986 | Bensinger | 604/6 |
| 4,685,900 | 8/1987 | Honard et al. | 604/5 |
| 4,687,808 | 8/1987 | Jarrett et al. | 604/5 |
| 4,692,411 | 9/1987 | Ghose | 604/5 |
| 4,810,632 | 3/1989 | McMillan | 435/7 |
| 5,122,112 | 6/1992 | Jones | 604/4 |
| 5,277,701 | 1/1994 | Christie et al. | 604/4 |

FOREIGN PATENT DOCUMENTS

| | | | |
|---|---|---|---|
| 0237659 | 9/1987 | European Pat. Off. | 604/4 |
| 0125872 | 9/1980 | Japan | 604/4 |
| 0276561 | 12/1986 | Japan | 604/4 |

OTHER PUBLICATIONS

Takahashi, et al, "A Simple and Rapid Method to Detect Platelet Associated IgG", Thromb. Res. (Oct. 1982) vol. 28, No. 1, pp. 11–17.

Faig, et al, "(Umulative Experience With a Simplified Solid–Phase Radio Immunoassay for the Detection of Bound Antiplatelet IgG, Serum Auto–,Allo–, and Drug–Dependent Antibodies", Blood, vol. 60, No. 4, (Oct. 1982), pp. 807–813.

Abams et al. (1983) Blood:62:108a.

(List continued on next page.)

*Primary Examiner*—Michael Powell Buiz
*Assistant Examiner*—At Nguyen

[57] ABSTRACT

Immune thrombocytopenic purpura is treated by removal of IgG and circulating immune complexes from the patient's blood. Removal is accomplished by exposing the blood or blood plasma to an immunoadsorbent capable of removing IgG and its complexes. The immunoadsorbent comprises a suitable solid phase coupled to a receptor capable of binding IgG and its complexes, such as protein A. The IgG and its complexes are then removed by the extracorporeal exposure of the patient's blood to the immunoadsorbent, either in a continuous or discontinuous process. In the continuous process, the blood is removed in a steady flow from the patient, separated into its plasma and cellular components, the plasma treated, and the combined cellular components and treated plasma reinfused to the patient. In the discontinuous method, a small volume of blood is removed from the patient, the entire volume separated into plasma and cellular components, the plasma treated, and the entire volume of treated plasma returned to the patient, usually after the cellular components have been returned.

25 Claims, 2 Drawing Sheets

OTHER PUBLICATIONS

Karpatkin (1985) Ann. N.Y. Acad. Sci. 437:58.
Walsh et al. (1984) N. Eng. J. Med. 311:635.
Bansal et al. (1978) Cancer 42:1–18.
Terman et al. (1981) N. Engl. J. Med. 305:1195–1200.
Jones et al. (1980) Cancer 46:675–684.
Ray et al. (1980) Cancer 45:2633–2638.
Besa et al. (1981) Am. J. Med 71:1035–1040.
Holohan et al. (1982) Cancer Res. 42:3663–3668.
Messerschmidt et al. (1982) Cancer Treat. Rep. 66:2027–2031.
MacKintosh et al. (1983) West. J. Med 139:36–40.
Snyder et al. (1982) J. Immunol. 128:2726–2730.
Jones et al. (1984) J. Biol. Resp. Mod. 3:286–292.
Kiprov et al. (1984) J. Biol. Resp. Mod. 3:341–346.
Kinet et al. (1986) Eur. J. Clin. Invest. 16:43–49 and 50–55.
Korec et al. (1984) J. Biol. Resp. Mod. 3:330–335.
Korec et al. (1986) Clin. Oncology 4:210–215.
Nilsson et al. (1981) Blood 58:38–44.
Jones et al. (1986) Plasma Therpay Transfus Technol. 7:333–349.

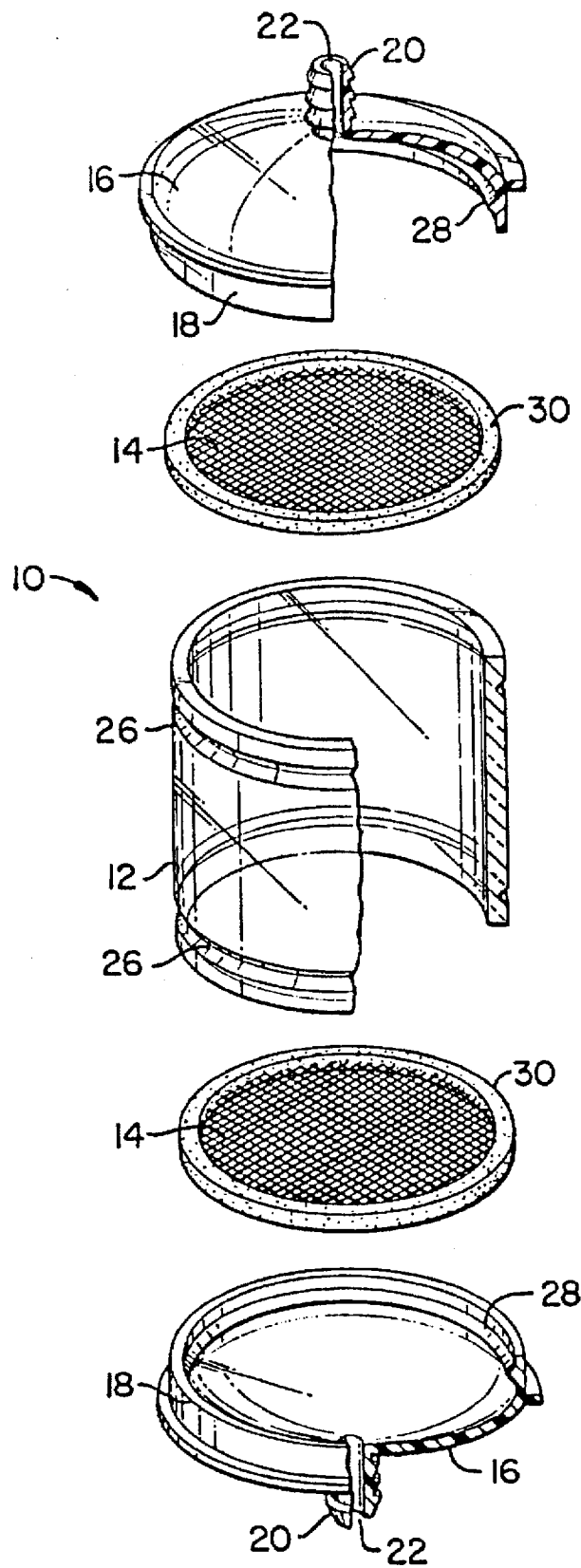
FIG._1.

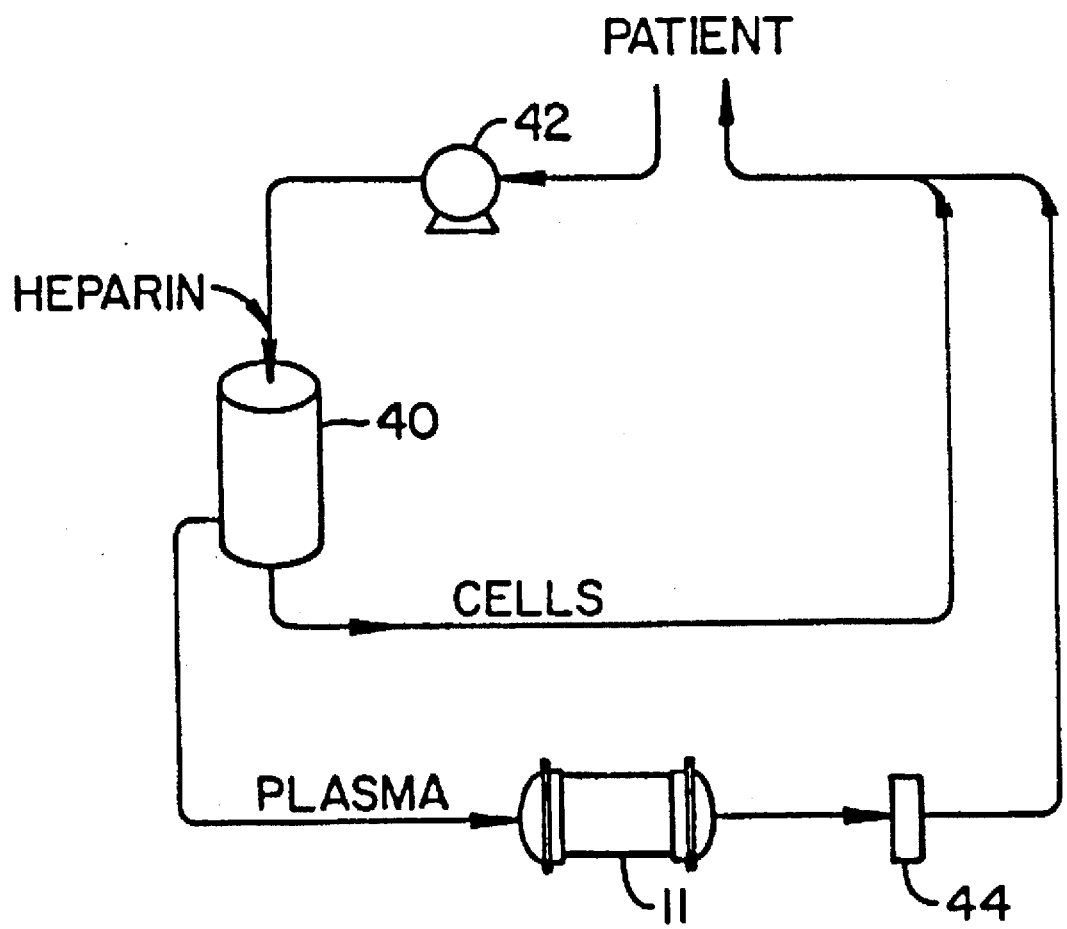
FIG._2.

METHOD FOR TREATING PATIENTS SUFFERING FROM IMMUNE THROMBOCYTOPENIC PURPURA

This is a Continuation of application U.S. Ser. No. 08/171,264, filed Dec. 21, 1993, abandoned, which is a con of U.S. Ser. No. 08/015,327 filed Feb. 9, 1993, abandoned, which is a con of U.S. Ser. No. 07/619,816, filed Nov. 29, 1990, abandoned, which is a con of U.S. Ser. No. 07/290,808, filed Dec. 22, 1988, abandoned, which is a con of U.S. Ser. No. 07/108,530, filed Oct. 15, 1987, abandoned.

BACKGROUND OF THE INVENTION

1. Field of the Invention

The present invention relates generally to the treatment of autoimmune disorders by extracorporeal plasma profusion to remove immunoglobulins and immune complexes. More particularly, the present invention relates to the treatment of immune thrombocytopenic purpura (ITP) by continuous or discontinuous plasma profusion using an immunoadsorbent capable of binding immunoglobulins and immune complexes.

Immune thrombocytopenic purpura (also referred to as idiopathic thrombocytopenic purpura) is a condition characterized by the appearance of lesions resulting from hemorrhage into the skin. ITP occurs in both and acute and chronic forms, and in both forms there are normal or increased numbers of megakaryocytes in the bone marrow, shortened platelet survival time, the presence of bound anti-platelet antibody, and the absence of lymphadenopathy.

Acute ITP is mainly a disorder of children which occurs following typical childhood infections, especially upper respiratory infections. Petechial hemorrhages and purpura, sometimes accompanied by hemorrhagic bullae in the oral cavity and gastrointestinal and genitourinary bleeding, occur abruptly. Platelet counts as low as 20,000/mm$^3$ and below are observed, with normal platelet counts being in the range from about 150,000–200,000/mm$^3$. In about 80% of the cases, the acute disease goes in to remission without treatment after a period of from about 2 to 6 weeks. In 10% of the cases, the patients will not recover and will develop a chronic ITP which is more often observed in adults.

Chronic ITP of adults is characterized occasionally by petechie, a tendency toward bruising, moderate bleeding after trauma, and platelet counts which are one-third to one-half of the normal value. The disease is characterized by cyclic remissions and relapses over long periods of time. Spontaneous recovery occurs in fewer than 10% of the patients.

Recently ITP has been reported in the sexually active homosexual community. While the origin of the disease may differ, the ITP syndrome in homosexuals is indistinguishable from the classic variety of chronic ITP with increased megakaryocytes in the bone marrow, absent splenomegaly, negative anti-nuclear antibodies, and no clinical disorder known to cause thrombocytopenia.

Presently, there are two accepted treatment modalities for chronic ITP. Treatment with corticosteroids is the treatment of choice. In patients where corticosteroid treatment is ineffective, splenectomies are the next treatment chosen. While such treatments are generally effective in a majority of ITP patients, approximately 5 to 20% of the patients with chronic ITP eventually become refractory to both treatment modalities.

For the above reasons, it would be desirable to provide alternate treatment modalities for chronic ITP. In particular, it would be desirable to provide a treatment method which could cure or provide remission for ITP patients who are refractory to other treatment methods.

2. Description of the Background Art

Multiple cases of immune thrombocytopenic purpura have been documented among sexually active homosexual males. See, Abrams et al. (1983) Blood:62:108a, and Karpatkin (1985) Ann. N.Y. Acad. Sci. 437:58. Deposition on platelets of either immune complexes or platelet-specific antibodies appears to be a causative factor in the disease Walsh et al. (1984) N. Eng. J. Med. 311:635.

Heat and formalin-treated *Staphylococcus aureus* Cowan I packed in a column has been employed to remove immune complexes from blood as a therapy for neoplastic disease. See, e.g., Bansal et al. (1978) Cancer 42:1–18; Terman et al (1981) N. Engl. J. Med. 305:1195–1200; Jones et al. (1980) Cancer 46:675–684; Ray et al. (1980) Cancer 45:2633–2638; Besa et al. (1981) Am. J. Med. 71:1035–1040; Holohan et al. (1982) Cancer Res. 42:3663–3668; Messerschmidt et al. (1982) Cancer Treat. Rep. 66:2027–2031; MacKintosh et al. (1983) West. J. Med. 139:36–40; Snyder et al. (1982) J. Immunol. 128:2726–2730; Jones et al. (1984) J. Biol. Resp. Mod. 3:286–292; and Kiprov et al. (1984) J. Biol. Resp. Mod. 3:341–346. Terman et al. (1981) N. Engl. J. Med. 305:1195–1200 describes extracorporeal plasma perfusion using an immunoadsorbent consisting of protein A entrapped within a charcoal matrix as a treatment of cancer patients. U.S. Pat. No. 4,614,513 teaches the extracorporeal removel of IgG and immune complexes as a treatment for cancer. Similar work is reported in Kinet et al. (1986) Eur. J. Clin. Invest. 16:43–49 and 50–55.

Korec et al. (1984) J. Biol. Resp. Mod. 3:330–335 and (1986) Clin. Oncology 4:210–215 describe the treatment of patients suffering from thrombotic thrombocytopenic purpura by extracorporeal removal of IgG and immune complexes with an agarose-protein A column. Nilsson et al. (1981) Blood 58:38–44 describe the extracorporeal removal of anti-factor IX antibodies using an agarose-protein A column.

SUMMARY OF THE INVENTION

The present invention is a method for treatment of patients suffering from immune thrombocytopenic purpura (ITP), which method can provide remission in patients who have proven resistant to conventional treatment, such as corticosteroid treatment and splenectomy. The treatment involves the extracorporeal removal of IgG and immune complexes from the blood. Such removal is effected by extracorporeal immunoadsorption, usually using a protein A immunoadsorbent. Other immunoadsorbent having receptors specific for IgG and/or immune complexes may also find use.

In the preferred embodiment, blood is withdrawn from the patient, separated into plasma and cellular components, and the plasma component perfused through the immunoadsorp column. Such immunoadsorbtion may be either continuous, with a continuous flow of blood being withdrawn, treated and returned to the patient while fresh blood continues to be drawn, or discontinuous, with a small volume of blood being withdrawn, treated in its entirety, and returned to the patient after the treatment is complete.

BRIEF DESCRIPTION OF THE DRAWINGS

FIG. 1 is an exploded view of an immunoadsorbent column useful with the method of the present invention.

FIG. 2 is a diagramatic representation of a system useful for continuous mode extracorporeal treatment of blood according to the present invention.

DESCRIPTION OF THE SPECIFIC EMBODIMENTS

Immune thrombocytopenic purpura (ITP) is treated by the specific removal of immunoglobulin G (IgG) and immune complexes containing IgG from the patient's blood. It is found that such removal lowers the level of platelet associated antibodies and Clq complexes, while simultaneously increasing the patient's platelet count. Clinical improvement has been observed in patients refractory to other forms of treatment, particularly those patients who displayed elevated levels of platelet-associated antibodies prior to such treatment.

The total amount of IgG and IgG-containing immune complexes removed during a single treatment procedure will depend largely on the level of IgG and its complexes initially present in the patient's blood. The amount removed may range from about 0.5 to 10.0 g, typically being about 0.5 to 1.5 g. These amounts relate to a percentage of removal in the range from about 2 to 30 percent (by weight), more usually in the range from about 2 to 5 percent (by weight).

The removal of IgG and its complexes is accomplished by exposing the patient's blood or blood plasma to an immunoadsorbent capable of such removal. The immunoadsorbent may incorporate a variety of receptors capable of binding to IgG and its complexes, such as protein A, anti-human IgG antibodies (particularly those directed against the $F_c$ region), rheumatoid factor (RF), the Clq portion of complement, conglutinin, blood platelets, and the like. Particularly preferred is the use of protein A, either in its purified form attached to a suitable solid phase or as a packed column of *Staphylococcus aureus* where the protein A is present on the cell membrane. Packed *Staphylococcus aureus* Cowan I may be prepared as described in detail in Jones et al. (1980) Cancer 46:675–684.

Having the desired receptor, immunoadsorbent columns may be prepared conventionally by coupling the receptor to a suitable solid phase column packing, such as agarose, available under the trade name Sepharose®, dextran, available under the trade name Sephadex®, cellulose, latex particles, polymethacrylate beads, polystyrene beads, silica particles, and the like. The preferred solid phase packing material is silica which is covalently bound to the receptor.

The solid phase silica may comprise virtually any form of particulate silica, including amorphous silicas, such as colloidal silica; silica gels, precipitated silicas, microcrystalline silicas, such as diatomites, and crystalline silicas, such as quartz. The silicas should have a particle size in the range from about 45 to 120 mesh, usually in the range from about 45 to 60 mesh.

In the preferred embodiment, the solid phase packing of the immunoadsorbent material will usually be formed from diatomite aggregates. Usually, the diatomite material will be calcined to remove any remaining organic material and to harden the surface of the aggregates in order to lessen breakage and degradation of the immunoadsorbent during use. The diatomite material consists primarily of silica (silicon dioxide) with lesser amounts of other minerals, including aluminum oxide, calcium oxide, magnesium oxide, ferric oxide, and the like. Usually, the diatomite material will comprise at least 80% silica, with less than 5% by weight of any other single mineral. Other impurities may be present in the diatomite, but care should be taken that such impurities are non-toxic and non-degradative to the biological fluid being treated. A particularly suitable solid phase-silica (diatomite) matrix may be obtained from the Mannville Corporation under the trade name Chromosorb®.

The receptor is covalently coupled to the solid-phase silica matrix by derivatizing the matrix to introduce active reactive functional groups, and reacting the derivatized matrix with a coupling agent or under chemical conditions which binds the receptor to the matrix. Exemplary protocols for such binding are as follows.

Amino groups may be introduced to the silica matrix as the reactive functional group by any suitable method. For example, the silica matrix is first acid washed, followed by extensive rinsing with water and drying. The acid washed silica is then reacted in a 5% to 10% solution of an aminosilane, such as λ-aminopropyltriethoxysilane, with the pH adjusted to about 3.0. After 2 hours at about 75° C., the silica matrix is again washed extensively with water and dried overnight at 100° C.

Carboxyl groups may be introduced to the silica matrix as the reactive functional group by further reacting the amino-derivatized material, as just described, with succinic anhydride as follows. The silica matrix is mixed with succinic anhydride in a suitable buffer, such as 0.5M phosphate buffer, and the pH adjusted to about 6.0. After 12 to 16 hours at room temperature, the silica matrix is extensively washed, and dried.

Hydroxyl groups (in addition to those hydroxyl groups occurring in the native structure of the matrix) may be introduced to the silica matrix by any suitable method. For example, the silica matrix is first acid washed, rinsed extensively with water, and dried. The acid washed silica is then reacted in a 5–10% solution of a silane such as λ-glycidoxypropyltrimethoxysilane. After a 2 hour incubation at 75° C., the silica matrix is again washed extensively with water and dried at 100° C.

Once the silica matrix has been derivatized with either amino and/or carboxyl groups, the protein A is introduced by reaction with a carbodiimide which forms a covalent link between the matrix and the protein A. The carbodiimide will have the formula:

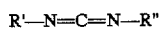

where R' and R" may be the same or different, being either alkyl, substituted-alkyl, benzyl, substituted-benzyl, or hydrogen. Alkyl or substituted-alkyl may be straight, branched or cyclic, and R will usually have fewer than 16 atoms, and six or fewer heteroatoms (i.e., other than carbon and hydrogen). If substituted-benzyl, R will usually have three or fewer substitutions which will typically be halogen atoms. Suitable carbodiimides are well known in the art. The preferred carbodiimide is 1-cyclohexyl-3-(2-morpholinoethyl)carbodiimide metho-p-toluenesulfonate.

The binding reaction for the amino-derivatized matrix is carried out under the following conditions. The protein A is mixed in water in the presence of the carbodiimide. The pH of the solution is adjusted to the range from 3.5 to 4.5, usually about 3.5, and the silica matrix is introduced and gently mixed for an extended period, usually about 5 to 30 hours, more usually about 20 to 25 hours at room temperature. The matrix is then extensively washed with water, dried, and acid washed at a pH from about 2.0 to 2.5, usually about 2.25, to remove labile protein and other substances which are non-covalently bound to the silica matrix. The material is then finally washed, dried and checked for the presence of pyrogens. A suitable test for the presence of pyrogens is the limulus ambeocyte lysate (LAL) test, commercially available as a kit from Marine Biologicals, Inc., P.O. Box 546, Marmora, N.J. 08222.

The binding process for the carboxyl-derivatized silica matrix is as follows. A carbodiimide (as above) is dissolved in water, and the solution is adjusted to a pH in the range from 3.5 to 4.5, usually about 3.5 pH. After introducing the silica matrix, the solution is gently mixed for an extended period, usually about 10 to 25 hours, more usually about 12 to 20 hours, at room temperature. The silica matrix is then removed and extensively washed with water. The protein A is then dissolved in water, the pH adjusted to the range from 3.5 to 4.5, usually about 3.5, and the silica matrix added and mixed for about 15 to 30 hours, usually about 20 to 25 hours at room temperature. The silica matrix is then removed and extensively washed with water. The protein A is then dissolved in water, the pH adjusted to the range from 3.5 to 4.5, usually about 3.5, and the silica matrix added and mixed for about 15 to 30 hours, usually about 20 to 25 hours at room temperature. The silica matrix is then extensively washed with water, dried, and washed one time in an acid wash (pH 2.0 to 2.5, usually about 2.25) to remove non-covalently bound protein A and other substances. The silica matrix is then washed a final time, and checked for pyrogens.

The binding process for the hydroxyl derivatized silica matrix is as follows. Cyanogen bromide is dissolved in water. The silica matrix is added to water and the pH is adjusted to 11.0. The cyanogen bromide solution is added to the silica matrix, the mixture is constantly stirred keeping the silica particles in suspension, and the pH is maintained between 11.0 and 11.5 by addition of NaOH until pH stabilization occurs. The activated silica matrix is extensively washed with water, mixed with a solution of protein A with the pH adjusted to 8.5–9.0, and mixed overnight at 25° C. After coupling, the matrix is washed extensively with water, dried and washed one time in an acid wash, pH 2.5, to remove non-covalently bound and acid labile protein A linkages. The silica matrix is washed a final time and checked for pyrogens.

The pH range of from 3.5 to 4.5 for binding of the protein A to the amino and/or carboxyl functionalities on the silica matrix is critical. Similarly, the binding of the protein A to the hydroxyl functionalities at a pH in the range from 8.5 to 9.0 is also critical. The efficiency of binding and the retained activity of the protein A both diminish as the pH deviates outside of these narrow ranges. Moreover, it has been found that a mild acid wash with a pH in the range from about 2.0 to 2.5 successfully removes non-covalently bound substances from the silica matrix, particularly cleaving labile protein A linkages. The acid treatment is thus important in achieving a stable immunoadsorbent material which is able to retain the IgG and IgG-complexes bound within the column and avoid loss of protein A into the plasma being treated.

Referring now to FIG. 1, the construction of a suitable cartridge 10 for containing the immunoadsorbent material just described is illustrated. The cartridge comprises a cylinder 12, a pair of retaining screens 14, and a pair of end caps 16. The end caps 16 each include a flange element 18 projecting from one surface thereof and a connector nipple 20 projecting from the other surface thereof. The connector nipple 20 includes an axial passage 22 therethrough to define inlet/outlet ports 24 through the end caps 16. The cylinder 12 includes an annular groove 26 at each end thereof. The flange element 18 on each end cap 16 includes a mating ring 28 on the inner cylindrical surface, which mating ring engages the annular groove 26 when the caps are placed over the end of cylinder 12. Each screen 14 includes a silicone gasket 30 around its circumference, which gasket serves as a sealing member between the end caps 16 and the cylinder 12. To assemble cartridge 10, a first screen 14 is placed over one end of the cylinder, and an end cap 16 is fitted over the screen 14. The cylinder 12 is then filled with the immunoadsorbent material, and the assembly of the cartridge is completed by placing the remaining screen 14 and end cap 16 into place. The dimensions of the cartridge 10 are not critical, and will depend on the desired volume of the immunoadsorbent material. The volume of cylinder 12 typically will be in the range from about 50 to 500 cc, having a diameter in the range from about 4 to 8 cm and a length in the range from about 5 to 10 cm.

A column 11 (FIG. 2) which comprises cartridge 10 containing a suitable volume of the immunoadsorbent material may be sterilized, typically with a gas steriliant such as ethylene oxide, and either used immediately or sealed and stored for later use. Prior to use, the column 11 will be washed with normal saline followed by a wash with normal saline containing heparin or other suitable anti-coagulant, such as acid citrate dextrose (ACD).

The column 11 may be used in either a continuous (on-line) or discontinuous (off-line) process for treating the patient. In the continuous process, a flow of blood is obtained from the patient, continually separated into its cellular and plasma components, and the plasma component run through the immunoadsorbent column. The combined cellular component and treated plasma component is then returned to the patient. Continuous procedures are useful for treating relatively large volumes of blood, usually in excess of 500 ml, more usually in excess of 1 liter, and often equaling the entire blood volume of the individual patient. As may be appreciated, the continuous process results in the removal of a high percentage of the IgG and IgG-associated immune complexes from the patient's blood, while the discontinuous process removes a much smaller portion.

A system suitable for the continuous removal of IgG and IgG complexes from a patient's perfused blood is illustrated in FIG. 2. The column 11 is connected to a cell separator 40 to receive separated plasma therefrom. The cell separator 40 may be a continuous flow separator, such as the Centry machine, available from COBE Labs, Golden, Colo., or may comprise semi-permeable membrane which allows passage of the plasma and blood proteins, but inhibits passage of the cellular elements of the blood. In case of a semi-permeable membrane, a blood pump 42 will be required to pass the blood through the membrane. Suitable blood pumps include tube and peristaltic pumps where blood is isolated from the pumping mechanism to prevent contamination. The blood plasma will pass through the column 11 at a rate in the range from about 10 to 20 ml/min., typically until a total blood plasma volume of at least 1 liter, usually at least 2 liters, has been passed. The blood plasma is then mixed with the blood cells from the cell separator 40, and the recombined blood reinfused to the patient. Typically, a microfilter 44 is provided at the outlet of the treatment column 11 to prevent passage of macroscopic particles which might be lost from the column 11.

Discontinuous treatment comprises removing a small volume of blood from the patient, typically in the range from 100 to 600 mls, more usually in the range from 400 to 500 mls, separating the entire volume of blood into cellular and plasmic components, returning the cellular components substantially immediately to the patient, contacting the plasma with the immunoadsorbent, typically by passage through the immunoadsorbent column 11 just described, and returning the treated plasma to the patient, usually within 15 to 60 minutes of removal. The use of the discontinuous method is often preferable since it has reduced side effects when compared to the continuous treatment method described previously.

The method of the present invention has been found to be particularly effective in those patients found to have elevated blood levels of platelet associated antibodies. Platelet associated antibodies are defined as those antibodies that are bound to platelets of the patient. ITP patients have a level of platelet associated antibodies typically in the range from about 5 ng/$10^6$ Plt to 50 ng/$10^6$ Plt. Those displaying the most favorable response to the treatment method of the present invention will usually have levels of platelet associated antibodies exceeding about 15 ng/$10^6$ Plt, more usually exceeding about 20 ng/$10^6$ Plt. After treatment with the method of the present invention, the level of platelet associated antibodies will drop, typically to about 10 ng/$10^6$ Plt or below.

The following experiments are offered by way of illustration, not by way of limitation.

EXPERIMENTS

Materials and Methods

Twenty-four sexually active homosexual males suffering from ITP were treated by plasma perfusion with commercially available protein A-silica columns sold under the trade name Prosorba® column by IMRE Corporation, Seattle, Wash. The columns are prepared by covalently attaching protein A (200 mg) to a silica matrix which has been previously derivatized with λ-aminopropyltriethoxysilane. Unbound protein A and other substances are removed by acid washing, as described in U.S. patent application Ser. No. 690,781, the disclosure of which is incorporated herein by reference.

Each treatment consisted of perfusion of 250 ml of plasma over the column followed by return of the treated plasma to the patient at a rate of 10 to 20 ml/min. Each treatment removed approximately 1 g of IgG and/or IgG containing circulating immune complex (CIC). CIC were preferentially removed. Patients were treated once per week for four weeks. If no substantial and sustained increases in platelet counts were observed (i.e., a doubling of the pretreatment platelet value), four additional treatments were administered on alternate days. Patients were monitored prior to and after treatment for platelet count, platelet-associated antibodies (immunoglobulin bound to the patient's isolated platelets), platelet-directed antibodies (free serum immunoglobulin which binds to heterologous donor platelets in vitro), and CIC. Antibody levels were assessed in an enzyme-linked immunosorbent assay (ELISA) as described by Gudino and Miller (1981) Blood 57:32, and the CIC in serum were quantitated using a C1q-CIC ELISA (Immunomedics, Inc., Newark, N.J.).

Results

Prior to treatment, the mean platelet count in this population (N=24) was 50,500±5,957/mm$^3$ (x̄±SEM). The platelet count increased significantly during the treatment in 14 (58%) of the patients. Peak counts of 108,929±14,601 platelets/mm$^3$ were attained at some point during the combined treatment and follow-up periods (P<0.01); however, at the completion of treatments the mean count was 83,714±13,645 platelets/mm$^3$. Platelet-associated antibody levels decreased significantly in the responding patients (Table 1). Levels of platelet-directed antibodies and CIC were not significantly different pre- and post-treatment, although a trend was observed showing a decrease over the course of the therapy (Table 1). Responses of four of the patients were transient (less than 2 weeks duration), while the responses of the other 10 responders were of greater than 2 weeks duration. In six of these 10 patients, the response lasted more than 6 months. Neither the platelet counts, platelet-associated antibodies, platelet-directed antibodies, nor CIC levels changed significantly during the treatment in the non-responding patients (Table 1).

TABLE 1

Platelet and Immunologic Parameters of ITP Treated Patients

|  | Pre-treatment | Post-treatment | Significance |
| --- | --- | --- | --- |
| Responders (N = 14) |  |  |  |
| Platelets/mm$^3$ | 49,929 ± 8,444 | 83,714 ± 13,645 | P = 0.039 |
| PAA (ng/$10^6$ Plt) | 32 ± 9 | 10 ± 4 | P = 0.043 |
| PDA (ng/$10^6$ Plt) | 44 ± 11 | 32 ± 10 | P = 0.442 |
| C1q-CIC (μg/ml) | 105 ± 23 | 60 ± 15 | P = 0.137 |
| Non-responders (N = 10) |  |  |  |
| Platelets/mm$^3$ | 51,300 ± 8,564 | 45,600 ± 9,330 | P = 0.658 |
| PAA (ng/$10^6$ Plt) | 11 ± 4 | 9 ± 4 | P = 0.725 |
| PDA (ng/$10^6$ Plt) | 40 ± 15 | 34 ± 10 | P = 0.743 |
| C1q-CIC (μg/ml) | 56 ± 16 | 56 ± 15 | P = 0.991 |

PAA = platelet-associated antibodies
PDA = platelet-directed antibodies
All values are means ± standards error (x̄ ± SEMn)
Significance determined by Fisher's test While the responding and non-responding patients started treatment with nearly identical platelet counts, the responding patients had significantly higher levels of platelet-associated antibodies at the initiation of treatments (P=0.087). These results suggest that platelet associated antibody production can be down-regulated, presumably in response to removal of IgG and/or IgG-containing CIC from the patient's plasma. Thus, extracorporeal immunoadsorption to remove CIC and IgG from plasma using an immunoadsorbent column appears to be an effective form of treatment for patients with ITP, particularly those having elevated levels of platelet-associated antibodies initially.

Although the foregoing invention has been described in some detail by way of illustration and example for purposes of clarity of understanding, it will be obvious that certain changes and modifications may be practiced within the scope of the appended claims.

What is claimed is:

1. A method for treating a patient suffering from immune thrombocytopenic purpura, wherein the patient has had a volume of blood removed and separated into cellular components and plasma, which method consists essentially of removing extracorporeally immunoglobulin G and immune complexes of immunoglobulin G from the patient's plasma by contacting the plasma with an immunoadsorbent comprising protein A bound to silica and infusing the cellular components and the resulting plasma into the patient, and optionally repeating said treatment.

2. A method as in claim 1, wherein the protein A is covalently bound to silica.

3. A method as in claim 1, wherein about 500 mg to about 1500 mg of immunoglobulin G and immune complexes of immunoglobulin G are removed from the patient's plasma.

4. A method as in claim 1, wherein, prior to the removing step, the patient had levels of platelet-associated antibodies exceeding 15 ng/$10^6$ Plt.

5. A method as in claim 4, wherein the removing step reduces the levels of platelet-associated antibodies in the patient to below 10 ng/$10^6$ Plt.

6. A method as in claim 1, wherein the immune thrombocytopenic purpura is refractory to treatment by corticosteroids or splenectomy.

7. A method as in claim 1, wherein the plasma is contacted with the protein A immunoadsorbent contained in a cartridge wherein the cartridge comprises a cylinder, a pair of retaining screens at the ends of the cylinder to retain the protein A immunoadsorbent, a pair of endcaps covering the retaining screens, an inlet port for the plasma at one endcap, and an outlet port for the plasma at the other endcap, wherein the extracorporeal removal of immunoglobulin G and immune complexes of immunoglobulin G is accomplished by passing the plasma into the cylinder through the inlet port and out through the outlet port.

8. A method for treating a patient suffering from immune thrombocytopenic purpura, wherein said method consists essentially of:

(a) drawing blood from the patient;

(b) separating the blood into cellular components and plasma;

(c) contacting the plasma with a protein A immunoadsorbent, wherein said protein A immunoadsorbent comprises protein A bound to silica;

(d) reinfusing the treated plasma and cellular components into the patient; and (e) optionally periodically repeating steps (a)–(d).

9. A method as in claim 8, wherein a preselected volume of blood is drawn from the patient, and the entire volume is separated and contacted prior to reinfusing into the patient.

10. A method as in claim 9, wherein the volume of blood drawn is in the range from about 100 to about 600 ml.

11. A method as in claim 8, wherein about 500 mg to about 1500 mg of immunoglobulin G and immune complexes of immunoglobulin G are removed from the patient's plasma.

12. A method as in claim 8, wherein, prior to the contacting step, the patient had levels of platelet-associated antibodies exceeding 15 ng/$10^6$ Plt.

13. A method as in claim 12, wherein the contacting step results in a reduction of the patient's levels of platelet-associated antibodies to below 10 ng/$10^6$ Plt.

14. A method as in claim 8, wherein the immune thrombocytopenic purpura is refractory to treatment by corticosteroids or splenectomy.

15. A method as in claim 8, wherein the plasma is contacted with the protein A immunoadsorbent contained in a cartridge wherein the cartridge comprises a cylinder, a pair of retaining screens at the ends of the cylinder to retain the protein A immunoadsorbent, a pair of endcaps covering the retaining screens, an inlet port for the plasma at one endcap, and an outlet port for the plasma at the other endcap, wherein contact of the plasma with the protein A immunoadsorbent is accomplished by passing the plasma into the cylinder through the inlet port and out through the outlet port.

16. A method for treating a patient suffering from immune thrombocytopenic purpura wherein said method consists essentially of:

(a) recovering plasma from the patient by withdrawing a preselected volume of blood and separating the blood into cellular components and plasma;

(b) contacting the plasma with an immunoadsorbent material comprising protein A bound to silica;

(c) reinfusing the plasma and cellular components into the patient; and (d) optionally periodically repeating steps (a) through (c).

17. A method as in claim 16, wherein the preselected volume is in the range from about 100 to 600 ml and the entire volume of plasma is contacted with the immunoadsorbent prior to reinfusion.

18. A method as in claim 16, wherein the preselected volume of blood is greater than 1000 ml and the volume of plasma is continuously contacted with the immunoadsorbent and reinfused into the patient while blood continues to be drawn.

19. A method as in claim 16, wherein patients having elevated levels of platelet-associated antibodies are preferentially selected for treatment.

20. A method as in claim 19, wherein the levels of platelet-associated antibodies are in excess of 15 ng/$10^6$ Plt.

21. A method as in claim 20, wherein the contacting step results in a reduction of the patient's levels of platelet-associated antibodies below 10 ng/$10^6$ Plt.

22. A method as in claim 16, wherein the steps are repeated at least four times at intervals of at least one day.

23. A method as in claim 16, wherein the plasma is contacted with the protein A immunoadsorbent contained in a cartridge wherein the cartridge comprises a cylinder, a pair of retaining screens at the ends of the cylinder to retain the protein A immunoadsorbent, a pair of endcaps covering the retaining screens, an inlet port for the plasma at one endcap, and an outlet port for the plasma at the other endcap, wherein contact of the plasma with the protein A immunoadsorbent is accomplished by passing the plasma into the cylinder through the inlet port and out through the outlet port.

24. A method as in claim 16, wherein the immune thrombocytopenic purpura is refractory to treatment by corticosteroids or splenectomy.

25. A method as in claim 16, wherein about 500 mg to about 1500 mg of immunoglobulin G and immune complexes of immunoglobulin G are removed from the patient's plasma.

\* \* \* \* \*

UNITED STATES PATENT AND TRADEMARK OFFICE
CERTIFICATE OF CORRECTION

PATENT NO. : 5,733,254

DATED : March 31, 1998

INVENTOR(S) : Frank R. Jones et al.

It is certified that error appears in the above-indentified patent and that said Letters Patent is hereby corrected as shown below:

Column 2, line 52 "immunoadsorbent" should read "immunoadsorbents."

Column 2, line 57 "immunoadsorp" should read "immunoadsorbent."

Column 2, line 58 "immunoadsorbtion" should read --immunoadsorption."

Signed and Sealed this

Eleventh Day of August 1998

Attest:

BRUCE LEHMAN

Attesting Officer

Commissioner of Patents and Trademarks